United States Patent
Ramirez de Agudelo

[19]

[11] Patent Number: 5,907,072
[45] Date of Patent: May 25, 1999

[54] MULTI-STAGE PROCESS FOR TREATING N-PARAFFINS

[75] Inventor: Maria Magdalena Ramirez de Agudelo, Los Teques, Venezuela

[73] Assignee: Intevep, S.A., Caracas, Venezuela

[21] Appl. No.: 08/982,711

[22] Filed: Dec. 2, 1997

Related U.S. Application Data

[60] Continuation-in-part of application No. 08/455,224, May 31, 1995, which is a division of application No. 08/292,832, Aug. 19, 1994, Pat. No. 5,523,272, and a continuation-in-part of application No. 08/902,186, Jul. 29, 1997, Pat. No. 5,821,188, which is a continuation of application No. 08/554,606, Nov. 6, 1995, Pat. No. 5,658,839, which is a division of application No. 08/353,812, Dec. 12, 1994, abandoned, which is a division of application No. 08/181,770, Jan. 21, 1994, Pat. No. 5,416,052.

[51] Int. Cl.[6] ................................. C07C 2/58
[52] U.S. Cl. ........................... 585/332; 585/331
[58] Field of Search ..................... 585/331, 332

[56] References Cited

U.S. PATENT DOCUMENTS

| | | | |
|---|---|---|---|
| 4,329,516 | 5/1982 | Al-Muddarris | 585/331 |
| 5,237,115 | 8/1993 | Makovec et al. | 585/331 |
| 5,254,748 | 10/1993 | Hensley et al. | 585/331 |
| 5,254,790 | 10/1993 | Thomas et al. | 585/331 |
| 5,416,052 | 5/1995 | De Agudelo et al. | 502/78 |
| 5,523,272 | 6/1996 | Ramirez De Agudelo et al. | 502/159 |
| 5,672,795 | 9/1997 | Vora et al. | 585/331 |

*Primary Examiner*—Walter D. Griffin
*Attorney, Agent, or Firm*—Bachman & LaPointe, P.C.

[57] ABSTRACT

A multi-stage process for treating n-paraffin feed is provided, including the steps of: (a) providing an n-paraffin feed; (b) contacting the n-paraffin feed with a dehydroisomerization catalyst under dehydroisomerization conditions so as to provide a dehydroisomerization product stream comprising n-paraffin, iso-paraffin, olefin and iso-olefin fractions; (c) mixing at least the iso-olefin fraction from the dehydroisomerization product stream with an alkyl alcohol to provide an etherification reaction feed; (d) contacting the etherification reaction feed with an etherification catalyst under etherification conditions so as to provide an etherification product stream comprising alkyl tert alkyl ether, n-paraffin, iso-paraffin and olefin fractions. (e) contacting an alkylation reaction feedstock comprising at least the iso-paraffin and olefin fractions from the etherification product stream with an alkylation catalyst under alkylation conditions so as to provide an alkylation product stream comprising alkylate and n-paraffin fractions; and (f) adding the n-paraffin fraction of the alkylation product stream to the n-paraffin feed of step (a).

6 Claims, 1 Drawing Sheet

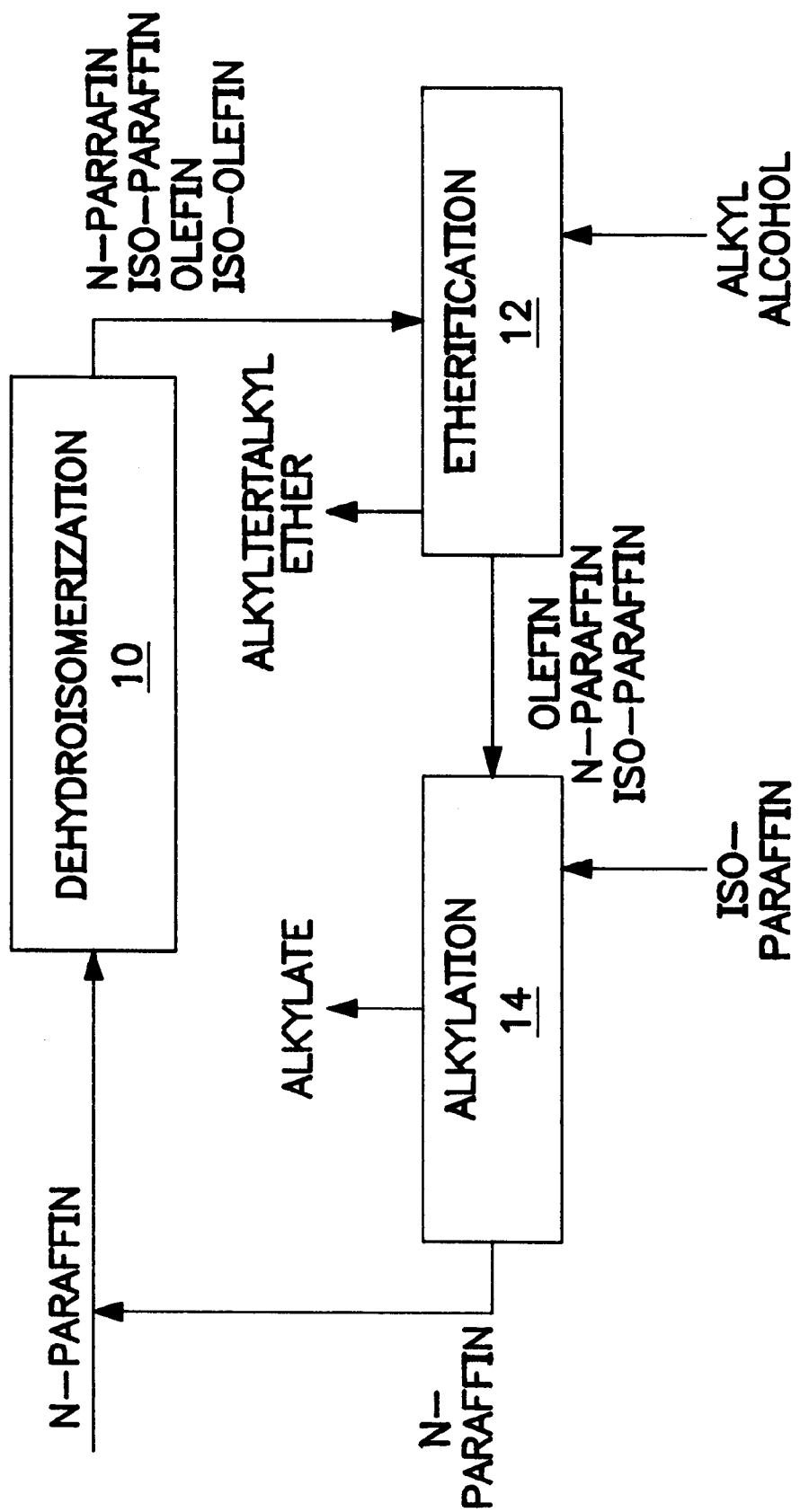

MULTI-STAGE PROCESS FOR TREATING N-PARAFFINS

CROSS REFERENCE TO RELATED APPLICATIONS

This application is a continuation-in-part of application Ser. No. 08/455,224 filed May 31, 1995 which in turn is a divisional application of application Ser. No. 08/292,832 filed Aug. 19, 1994, now U.S. Pat. No. 5,523,272 issued Jun. 4, 1996, and a continuation-in-part of application Ser. No. 08/902,186 filed Jul. 29, 1997, now U.S. Pat. No. 5,821,188, which is a continuation of application Ser. No. 08/554,606 filed Nov. 6, 1995, now U.S. Pat. No. 5,658,839, which is a divisional application of application Ser. No. 08/353,812 filed Dec. 12, 1994, now abandoned, which is a divisional application of application Ser. No. 08/181,770 filed Jan. 21, 1994, now U.S. Pat. No. 5,416,052 issued May 16, 1995.

BACKGROUND OF THE INVENTION

The present invention relates to a multi-stage process for treating n-paraffin feed and, particularly; to a cyclical process for treating an n-paraffin feed through a dehydroisomerization stage, an etherification stage, and an alkylation stage, wherein the reaction product of the alkylation stage includes a portion which is recycled to the feed for the first stage.

Various processes exist in the prior art for converting n-paraffin and other feeds into more useful and valuable products such as iso-paraffins, alkyl tert alkyl ethers, alkylate and the like.

Heretofore, each of these processes has been carried out individually, and therefore has required separate facilities and/or equipment for carrying out each process.

The need remains for a process wherein a feed is treated at sequential stages to provide various desired products, without requiring separate facilities, transportation, storage and the like for each process.

It is therefore the primary object of the present invention to provide a multi-stage process wherein an n-paraffin feed and resulting reaction products are treated sequentially at a number of different reaction zones, and the final reaction product includes a fraction which is recycled to the first reaction zone.

Other objects and advantages of the present invention will appear hereinbelow.

SUMMARY OF THE INVENTION

In accordance with the present invention, the foregoing objects and advantages of the present invention have been readily attained.

According to the invention, a multi-stage process for treating n-paraffin feed is provided, which process comprises the steps of: (a) providing an n-paraffin feed; b) contacting the n-paraffin feed with a dehydroisomerization catalyst under dehydroisomerization conditions so as to provide a dehydroisomerization product stream comprising n-paraffin, iso-paraffin, olefin and iso-olefin fractions; (c) mixing at least said iso-olefin fraction from said dehydroisomerization product stream with an alkyl alcohol to provide an etherification reaction feed; (d) contacting said etherification reaction feed with an etherification catalyst under etherification conditions so as to provide an etherification product stream comprising alkyl tert alkyl ether, n-paraffin, iso-paraffin and olefin fractions; (e) contacting an alkylation reaction feedstock comprising at least said iso-paraffin and olefin fractions from said etherification product stream with an alkylation catalyst under alkylation conditions so as to provide an alkylation product stream comprising alkylate and n-paraffin fractions; and (f) adding said n-paraffin fraction of said alkylation product stream to said n-paraffin feed of step (a).

BRIEF DESCRIPTION OF THE DRAWINGS

A detailed description of preferred embodiments of the invention follows, with reference to the attached drawing which schematically illustrates a multi-stage process in accordance with the present invention.

DETAILED DESCRIPTION

The present invention relates to a multi-stage process for treating an n-paraffin feed sequentially at a dehydroisomerization reaction zone, an etherification reaction zone and an alkylation reaction zones and wherein a fraction of the product from the alkylation reaction zone is recycled to the initial or dehydroisomerization reaction zone.

The attached figure schematically illustrates such a process, starting with an n-paraffin feed to a dehydroisomerization zone 10, which provides a dehydroisomerization product stream comprising n-paraffin, iso-paraffin, olefin and iso-olefin fractions. At least the iso-olefin fraction of the dehydroisomerization product stream is mixed with an alkyl alcohol so as to provide an etherification reaction feedstock, and is fed to an etherification zone 12. The product of etherification zone 12 comprises an alkyl tert alkyl ether product, n-paraffin, iso-paraffin and olefin fractions. In accordance with the process of the present invention, at least the olefin and iso-paraffin fractions are fed to alkylation zone 14, from which a product stream is provided comprising an alkylate and an n-paraffin fraction. In further accordance with the process of the present invention, and as illustrated, the n-paraffin fraction is then recycled to the feed to zone 10 so as to advantageously provide a cyclical multi-stage process.

In accordance with the invention, zone 10 is a dehydroisomerization zone wherein the n-paraffin feed is contacted with a dehydroisomerization catalyst under dehydroisomerization conditions so as to provide the desired product stream including n-paraffin, iso-paraffin, olefin and iso-olefin. The dehydroisomerization catalyst may be any desired catalyst, but may preferably be a modified mordenite zeolite catalyst modified with Pt and a promoter selected from the group consisting of Group IIB metals, Group IVA metals, Group VIB metals and mixtures thereof. Such catalysts are thoroughly described in U.S. Pat. No. 5,416,052 and 5,658,839 to De Agudelo et al.

Dehydroisomerization conditions are preferably selected so as to provide the desired n-paraffin, iso-paraffin, olefin and iso-olefin product stream. Suitable dehydroisomerization conditions may preferably include a paraffin space velocity of between about 0.1 and about 1000 $h^{-1}$, a hydrogen to paraffin ratio of between about 0.1 and about 30, and a temperature of between about 250° C. and about 800° C. More preferably the dehydroisomerization process conditions include a paraffin space velocity of between about 0.1 and about 250 $h^{-1}$, a hydrogen to paraffin ratio of between about 1 and about 15, and a process temperature of between about 500° C. and about 600° C.

Reaction zone 12 preferably includes an etherification catalyst, preferably an acidic ion exchange resin having at least a first active metal phase, preferably palladium. As described in U.S. Pat. No. 5,523,272 to Ramirez De Agudelo et al., the etherification catalyst may suitably be provided so as to resist deactivation from sulfur, if sulfur is present in the feed. This catalyst is suitable with feed having sulfur content up to about 300 ppm (wt). In this instance, the preferred etherification catalyst is an acidic ion exchange resin consisting essentially of a macroporous polystyrene resin crosslinked with divinylbenzene with a degree of crosslinking of between about 5% to about 65%; a palladium first metal phase supported on the resin; and a sulfur inhibiting second metal phase supported on the resin wherein the second metal phase is selected from the group consisting of metal having a d5 electron configuration, metals having a d10 electron configuration, and mixtures thereof and wherein the second metal phase has a stronger attraction for electrons than the first metal phase so as to inhibit sulfur deactivation of the first metal phase, and wherein the first metal phase is present in an atomic ratio to the second metal phase of between about 1:20 to about 1:0.1. The aforesaid U.S. Pat. No. 5,523,272 further describes such a catalyst and is incorporated herein by reference.

Etherification in zone 12 is preferably carried out under suitable conditions such that the reaction feedstock is converted to alkyl tert alkyl ether, as well as olefin, paraffin and iso-paraffin fractions. Preferable conditions include a pressure of between about 10 bars and about 25 bars, a temperature of between about 40° C. and about 90° C. and a space velocity of between about 0.5 $h^{-1}$ and about 5.0 $h^{-1}$.

Alkylation in zone 14 is preferably carried out using an alkylation catalyst and under alkylation process conditions which are well known to those of ordinary skill in the art so as to provide a product stream including alkylate, and n-paraffin which, as set forth above, is recycled to the feed to dehydroisomerization zone 10 in accordance with the process of the present invention.

Suitable n-paraffin feed includes any combination or mixture of n-paraffins such as $n-C_4-n-C_6$ and the like. Feed of n-butane to zone 10 will provide a product stream of n-butane, iso-butans, n-butene and iso-butene. At least the iso-butene fraction of this product stream is preferably fed in accordance with the invention to zone 12, where it is mixed with an alkyl alcohol such as MeOH so as to provide the desired etherification reaction feedstock. In this instance, the product stream from zone 12 would include methyl tert butyl ether (MTBE), n-butene, n-butane and iso-butane. At least the n-butene and iso-butane fractions are preferably fed to zone 14 for alkylation as desired, and additional iso-butane may be added to zone 14, if necessary so as to provide the desired alkylation conditions. In this instance, the product stream would include alkylate such as 2,2 dimethylbutane, and n-butane, and the n-butane is preferably recycled into the feed to zone 10 so as to advantageously provide for cyclical multi-stage reactions as desired in accordance with the present invention.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

What is claimed is:

1. A multi-stage process for treating n-paraffin feed, comprising the steps of:

(a) providing an n-paraffin feed;
    (b) contacting the n-paraffin feed with a dehydroisomerization catalyst comprising a modified mordenite zeolite catalyst modified with Pt and a promoter selected from the group consisting of Group IIB metals, Group IVA metals, Group VIB metals and mixtures thereof under dehydroisomerization conditions so as to provide a dehydroisomerization product stream comprising n-paraffin, iso-paraffin, olefin and iso-olefin fractions;
    (c) mixing at least said iso-olefin fraction from said dehydroisomerization product stream with an alkyl alcohol to provide an etherification reaction feed;
    (d) contacting said etherification reaction feed with an etherification catalyst under etherification conditions so as to provide an etherification product stream comprising alkyl tert alkyl ether, n-paraffin, iso-paraffin and olefin fractions;
    (e) contacting an alkylation reaction feedstock comprising at least said iso-paraffin and olefin fractions from said etherification product stream with an alkylation catalyst under alkylation conditions so as to provide an alkylation product stream comprising alkylate and n-paraffin fractions; and
    (f) adding said n-paraffin fraction of said alkylation product stream to said n-paraffin feed of step (a).

2. A process according to claim 1, further comprising the step of adding additional iso-paraffin to said alkylation reaction feedstock.

3. A process according to claim 1, wherein said dehydroisomerization conditions comprise a paraffin space velocity of between about 0.1 and about 1000 $h^{-1}$, a hydrogen to paraffin ratio by volume of between about 0.1 and about 30, and a temperature of between about 250° C. and about 800° C.

4. A process according to claim 1, wherein said etherification catalyst comprises an acidic ion exchange resin and a palladium metal phase supported on the resin.

5. A process according to claim 1, wherein said etherification reaction feedstock contains sulfur in an amount up to about 300 ppm, and wherein said etherification catalyst comprises:

an acidic ion exchange resin consisting essentially of a macroporous polystyrene resin crosslinked with divinylbenzene with a degree of crosslinking of between about 5% to about 65%;
    a palladium first metal phase supported on the resin; and
    a sulfur inhibiting second metal phase supported on the resin wherein the second metal phase is selected from the group consisting of metals having a d5 electron configuration, metals having a d10 electron configuration, and mixtures thereof and wherein the second metal phase has a stronger attraction for electrons than the first metal phase for inhibiting sulfur deactivation of the first metal phase, wherein the first metal phase is present at an atomic ratio to the second metal phase of between about 1:20 to about 1:0.1.

6. A process according to claim 1, wherein said etherification conditions comprise a pressure of between about 10 bars and about 25 bars, a temperature of between about 40° C. and about 90° C., and a space velocity of between about 0.05 $h^{-1}$ and about 5.0 $h^{-1}$.

* * * * *

UNITED STATES PATENT AND TRADEMARK OFFICE
CERTIFICATE OF CORRECTION

PATENT NO. : 5,907,072
DATED : MAY 25, 1999
INVENTOR(S) : MARIA MAGDALENA RAMIREZ DE AGUDELO

It is certified that error appears in the above-identified patent and that said Letters Patent is hereby corrected as shown below:

COLUMN 4, CLAIM 6, LINE 62, DELETE "0.05" AND INSERT --0.5--.

Signed and Sealed this

Twenty-third Day of November, 1999

Attest:

Q. TODD DICKINSON

*Attesting Officer*     *Acting Commissioner of Patents and Trademarks*